United States Patent [19]

Brewer

[11] Patent Number: 4,928,830
[45] Date of Patent: May 29, 1990

[54] SUCTIONING SUPPLY KIT

[75] Inventor: Cecil C. Brewer, Missouri City, Tex.

[73] Assignee: Board of Regents, The University of Texas System, Austin, Tex.

[21] Appl. No.: 265,389

[22] Filed: Oct. 31, 1988

[51] Int. Cl.⁵ .............................................. B65D 71/00
[52] U.S. Cl. ................................... 206/570; 206/571; 206/363; 206/364; 206/438
[58] Field of Search ............... 206/223, 278, 361, 363, 206/364, 438, 439, 470, 471, 562, 563, 564, 570, 571, 820

[56] References Cited

U.S. PATENT DOCUMENTS

| | | | |
|---|---|---|---|
| 3,524,690 | 8/1970 | Gurney | 206/364 |
| 3,886,946 | 6/1975 | Hyde | |
| 3,892,314 | 7/1975 | Semp | 206/363 |
| 3,993,223 | 11/1976 | Welker, III et al. | 206/820 |
| 4,085,845 | 4/1978 | Perfect | 206/564 |
| 4,135,868 | 1/1979 | Schainholz | 206/438 |
| 4,170,300 | 10/1979 | Pick | 206/365 |
| 4,226,328 | 10/1980 | Beddow | 206/364 |
| 4,338,930 | 7/1982 | Williams | |
| 4,405,047 | 9/1983 | Barba | 206/223 |
| 4,436,205 | 3/1984 | Horii | 206/820 |
| 4,466,973 | 8/1984 | Rennie | |
| 4,484,577 | 11/1984 | Sackner et al. | |
| 4,502,482 | 3/1985 | DeLuccia | |
| 4,512,475 | 4/1985 | Federighi | 215/32 |
| 4,523,679 | 6/1985 | Paikoff et al. | 206/570 |
| 4,534,342 | 8/1985 | Paxa | |
| 4,573,576 | 3/1986 | Krol | 206/438 |
| 4,601,713 | 7/1986 | Fugua | |
| 4,632,112 | 12/1986 | Matthews | |
| 4,677,978 | 7/1987 | Melker | |
| 4,696,296 | 9/1987 | Palmer | |
| 4,763,791 | 8/1988 | Halverson et al. | 206/570 |
| 4,767,008 | 8/1988 | Warnecke et al. | 206/570 |
| 4,784,267 | 11/1988 | Gessler et al. | 206/438 |
| 4,811,847 | 3/1989 | Reif et al. | 206/364 |

OTHER PUBLICATIONS

Bard-Parker REGU-VAC "Suction Kit 'N Cup".
Superior Healthcare Group Inc. "Suction Catheter Kit".
Concord Laboratories, Inc. "No Pour Pak Suction Kit".
LEXPAT Search Report.

*Primary Examiner*—David T. Fidei
*Attorney, Agent, or Firm*—Arnold, White & Durkee

[57] ABSTRACT

A kit for use in performing one or more suctioning procedures. The kit includes a tray for holding suctioning supplies, and one or more supply units contained within the tray. Each supply unit includes the following suctioning supplies: a pair of surgical gloves, an ampule containing a saline solution, a suction catheter, a lubricating gel, and a disposable bottle containing water. The suctioning supplies are removably disposed within the tray.

27 Claims, 4 Drawing Sheets

SUCTIONING SUPPLY KIT

BACKGROUND OF THE INVENTION

1. Field of the Invention

This invention relates to a kit for use in connection with suctioning procedures used in hospitals, clinics and other health care facilities.

2. Description of the Related Art

Medical suctioning procedures generally involve the cleaning of body passages (e.g., nasal passage or trachea), which may have become clogged with mucus or other matter, by suctioning such matter out of the passage to a remote disposal chamber. Typically, the medical technician attaches the appropriate end of a suctioning catheter to the connecting tubing of a suction unit. Such suction units are often mounted to a bedside wall in a hospital or medical office. The other end of the catheter is inserted into the patient's passage which is to be suctioned. The suction unit is then activated to withdraw the clogging matter from the passage. The catheter is then withdrawn.

If further suctioning of the passage is needed, the insertion tip of the catheter is typically submerged into a reservoir of water so that the water is suctioned through the catheter and suction unit to cleanse the interior surfaces. The catheter is then reinserted into the passage for further suctioning. This procedure may be repeated as necessary.

When suctioning has been completed and the catheter and suctioning unit cleansed for the final time, the catheter is detached from the suction unit connecting tubing, and usually discarded. The reservoir used to hold the irrigant water should also be discarded since it will have been contaminated by contact with the catheter.

A saline solution (or other appropriate solution) may be inserted into the patient's body passage prior to suctioning to loosen the matter to be withdrawn, thus facilitating thorough cleansing of the passage. This is typically done in tracheostomy suctioning procedures by squirting such a saline solution into the trachea through the surgical opening in the patient's neck.

In connection with some suctioning procedures, the exterior surface of the catheter is often lubricated prior to insertion into the passage. Sometimes, sufficient lubrication may be obtained by simply submerging the insertion tip of the catheter in water. However, in some procedures, such as nasal suctioning, more effective lubrication is needed, and the catheter may accordingly be coated with a gel.

It is apparent from the discussion above that various supplies, in addition to the actual suction unit, are required for performing a suctioning procedure. For example, a suction catheter is needed for insertion into the passage, and a reservoir with water is required for cleansing of the interior portion of the catheter and suction unit during and following each procedure. In some procedures, a saline solution is needed, as well as means for injecting the solution into the passage prior to suctioning. Also in some procedures, a lubricating gel (or water for lubrication) is needed to coat the catheter prior to insertion into the passage. Furthermore, as with all medical procedures, risk of infection should be guarded against, and, thus, the technician should wear surgical gloves during the suctioning procedure.

Typically, the technician must gather all of these supplies prior to each suctioning procedure, a time-consuming task particularly considering the frequency with which such procedures are performed in most hospitals. It is accordingly an object of the present invention to address the shortcomings of the prior techniques.

SUMMARY OF THE INVENTION

In accordance with one aspect of the present invention, a kit for use in performing a suctioning procedure is provided. The kit includes a tray and suctioning supplies removably disposed within the tray. The suctioning supplies include a pair of surgical gloves, an ampule containing a saline solution, a suction catheter, a lubricating gel, and a disposable bottle containing water. The lubricating gel may be provided, for example, in a foil pack or other suitable container or dispenser.

The term "ampule" is used broadly to include any container having means for injecting the saline solution into the passage to be suctioned. For example, the ampule may be a squeezable plastic tube, which may be punctured or clipped to provide an opening through which the solution contained within will flow upon squeezing of the tube.

Preferably, the surgical gloves, saline solution, suction catheter, lubricating gel, and water are provided in all embodiments of the kit in a sterile condition prior to use to minimize risk of infection. The lubricating gel is preferably water-soluble as is standard in most suctioning procedures.

It should be appreciated that this embodiment provides a complete set of supplies for performing a single suctioning procedure, adaptable to a wide variety of applications. The technician may thus have all the supplies needed for such procedures at his convenient disposal. It is envisioned that the technician will use the kit by putting on the surgical gloves and attaching the suction catheter to a suction unit (e.g., on a bedside wall) via the suction unit's connecting tubing. If the patient's passage to be suctioned requires loosening of matter, the technician may take the ampule from the kit and squeeze the saline solution into the passage. If the catheter needs lubrication for ease of insertion into the passage, the technician may submerge the tip of the catheter into the bottle of water. If greater lubrication is needed, the technician may coat the exterior surface of the catheter with the lubricating gel.

The catheter may then be inserted into the passage and suctioning may be commenced. During suctioning, the catheter may be periodically removed from the passage and inserted into the bottle of water for cleansing the interior of the catheter, connecting tubing, and suction unit. The bottle of water may thus serve as both a supply and reservoir of irrigant for the suctioning procedure.

After suctioning is completed and the catheter is inserted into the water bottle a final time for cleansing of the suction unit, the suctioning supplies may be discarded.

Preferably, the tray includes compartments cooperatively configured to hold the suctioning supplies. The suctioning supplies are accordingly disposed within the compartments. This embodiment provides the advantage of maintaining the supplies in a neat and organized fashion. The tray may include a cover cooperatively configured to cover the tray. This provides portability for the kit without risk of the supplies falling out of the tray. The cover is preferably hinged to the tray to provide easy opening and closing of the kit.

In a preferred embodiment, the kit includes a sealed pouch for holding the gloves. A sealed pouch may also be provided for holding the catheter. Alternatively, a single sealed pouch may be provided for holding both the catheter and gloves. Preferably, the interior of the sealed pouch is sterile and a sterile drape is included in the pouch. The drape may be made of paper or other material and may be used by the technician as a sterile field on which to place the suctioning supplies during a suctioning procedure. The drape may also be folded and used as an envelope in the pouch to hold the gloves and/or catheter therein.

In another preferred embodiment, the bottle containing water includes a mouth, a cap cooperatively configured with the mouth for covering the bottle, and a water tight and nonresealable seal between the mouth and the cap. By "nonresealable" it is meant that once the water tight seal is initially broken and the cap removed, a water tight seal can not again be achieved between the mouth and the cap. This provides some quality assurance against reusing a contaminated water bottle after use. During irrigation of the catheter and suction unit, the water in the irrigant reservoir bottle often becomes contaminated due to germs from the catheter. Thus, the reservoir container should be discarded after each use. It is believed that providing a nonresealable bottle to serve as the reservoir will decrease the risk that the reservoir will be inadvertently or carelessly reused.

In accordance with another aspect of the present invention, a kit for use in performing a series of suctioning procedures is provided. The kit includes a tray and a series of supply units removably disposed within the tray. Each supply unit comprises suctioning supplies including a pair of surgical gloves, an ampule containing a saline solution, a suction catheter, a lubricating gel, and a disposable bottle containing water.

As will be appreciated by those having skill in the art, this aspect of the present invention provides the technician with supplies for performing several cycles of suctioning procedures. Preferably the number of supply units is eight, although essentially any number could be selected. Eight would seem to provide a convenient number, since medical personnel performing suctioning procedures routinely serve eight hour shifts and may perform one procedure on a patient each hour. This being the case, the kit would be exhausted following each shift and could be discarded, thereby providing convenience and quality control.

The preferred features discussed above in connection with the single procedure kit are also applicable to the multiple procedure kit.

BRIEF DESCRIPTION OF THE DRAWINGS

FIG. 6A shows the bottle with the cap sealed over the mouth. FIG. 6B shows the bottle with the cap removed from the mouth.

DETAILED DESCRIPTION OF THE PREFERRED EMBODIMENT

Figure 1:
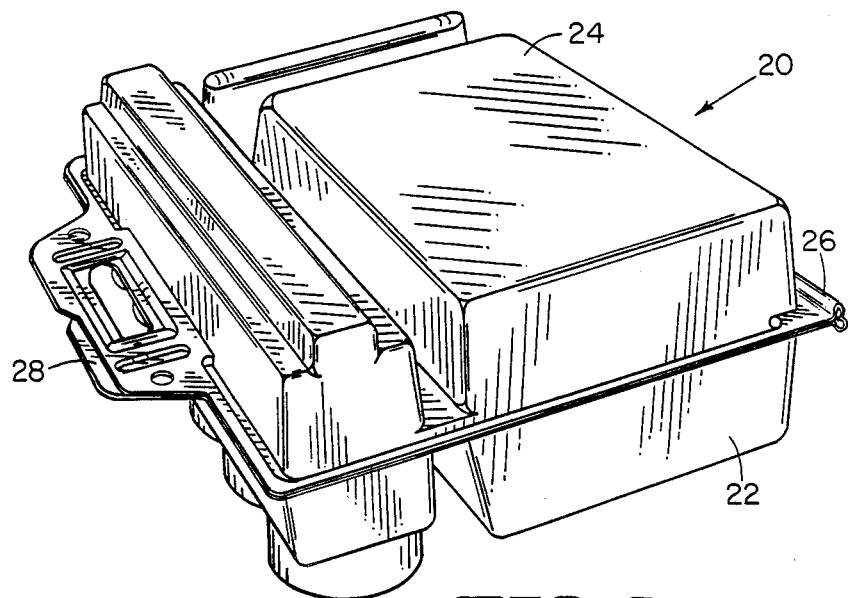
FIG. 1 is a perspective view of a kit in accordance with a preferred embodiment of the present invention, the kit being closed.
Figure 2:
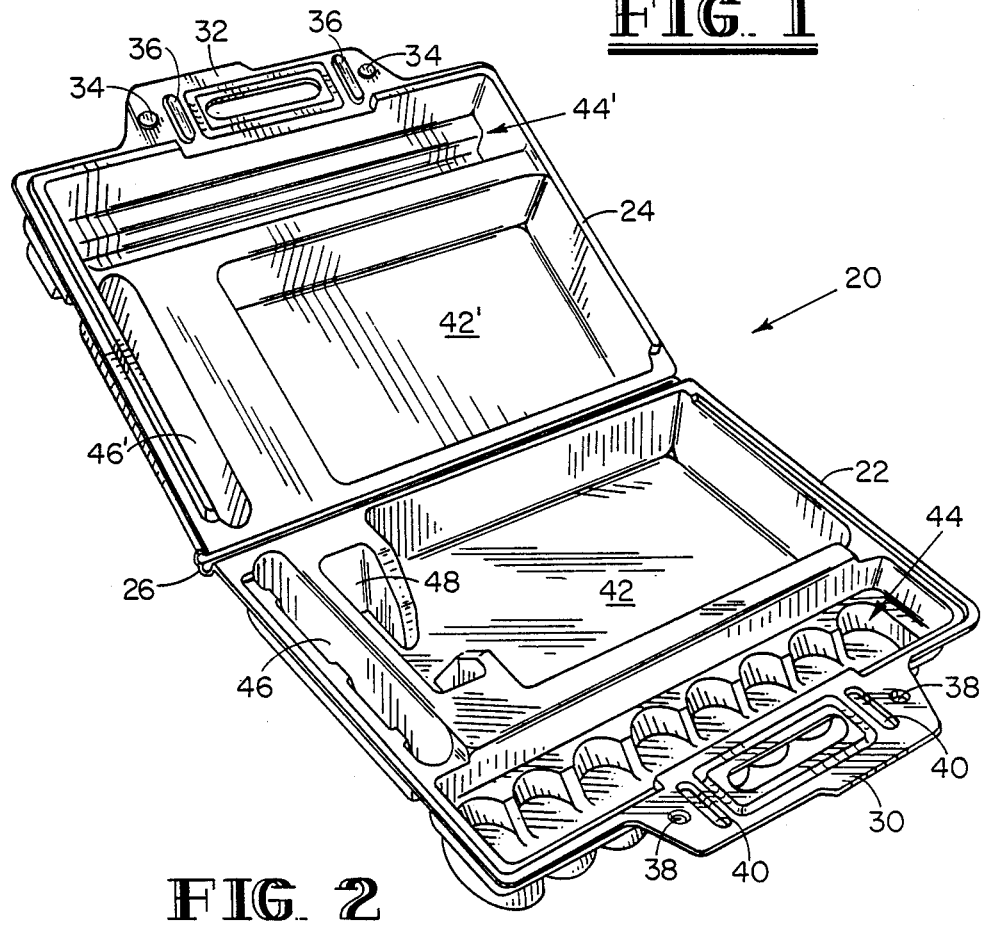
FIG. 2 is a perspective view of the same kit, the kit being open and having all suctioning supplies removed therefrom.
Figure 3:
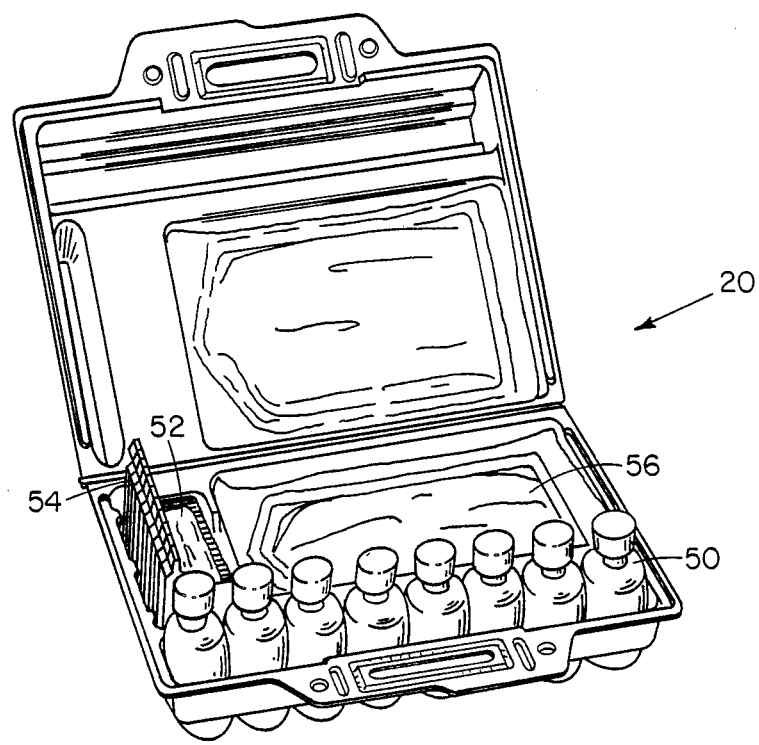
FIG. 3 is a perspective view of the same kit, the kit being open and having all suctioning supplies contained therein.

Referring to FIGS. 1-3, a preferred embodiment of a suctioning supply kit 20 as provided by the present invention is shown.

FIG. 1 shows the kit 20 in its closed position. The kit 20 includes a tray 22 for holding suctioning supplies therein, and a cover 24 cooperatively configured with the tray for covering the tray. In the preferred embodiment, the cover 24 is hinged to the tray 22 by hinge 26 so that the kit 20 may be easily opened and closed.

The kit 20 also preferably includes a handle 28 for carrying the kit. As best shown in FIG. 2, the handle may be formed by providing a handle section 30 integral with tray 22 along the edge opposite hinge 26. Similarly, a handle section 32 integral with cover 24 may be provided along the edge opposite hinge 26. Handle sections 30 and 32 are cooperatively configured such that they join to form the handle 28 upon closing the kit 20 (see FIG. 1).

Means for locking the tray 22 and cover 24 together are provided in the form of projections 34 and 36 in handle section 32 cooperatively configured with recesses 38 and 40 in handle section 30. When closing the kit 20, recesses 38 and 40 receive projections 34 and 36 to provide releaseably locking engagement between cover 24 and tray 22.

The tray 22 and cover 24 are preferably made of a flexible plastic material to provide durability and light weight portability.

As best shown in FIGS. 2 and 3, the tray 22 preferably includes compartments cooperatively configured to hold suctioning supplies. In one preferred embodiment, the following compartments are provided: a pouch compartment 42; eight water bottle compartments 44; an ampule compartment 46; and a foil pack compartment 48. The cover 24 includes cooperatively dimensioned recesses 42', 44', and 46' to accommodate the supplies when the kit 20 is closed.

FIG. 3 shows the kit having the suctioning supplies disposed within their respective compartments. Preferably, the kit 20 includes eight supply units. Each supply unit includes the following suctioning supplies: a disposable bottle 50 containing water; a foil pack 52 containing lubricating gel; an ampule 54 containing a saline solution; and a sealed pouch 56 containing an envelope which holds a pair of surgical gloves and a suction catheter. Preferably, the water, lubricating gel, saline solution, envelope, surgical gloves, suction catheter, and the interior of the sealed pouch are all sterile prior to use. The lubricating gel is preferably water-soluble.

Figure 4:
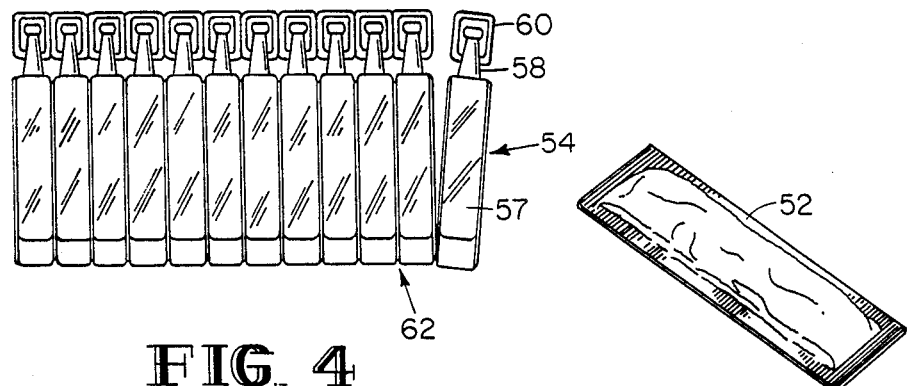
FIG. 4 is a side view of ampules containing saline solution as provided in the kit.

FIG. 4 shows the ampules 54 containing saline solution. Each ampule includes a body section 57, a nozzle 58, and a cap 60 releaseably sealed over the nozzle 58. The ampules 54 are preferably made of plastic and joined together at adjacent edges 62 to form a pack. Each ampule can be removed from the pack by breaking it away from the adjacent ampule as shown in FIG. 4. The cap 60 can then be removed from the nozzle 58, and the body section 56 can be squeezed to squirt the saline solution out of the nozzle. Preferably, twelve ampules are provided (instead of eight) for extra saline solution if needed.

Figure 5:
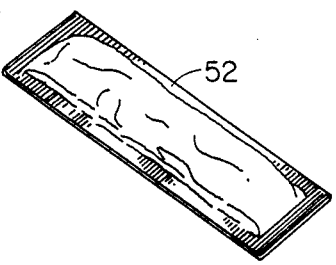
FIG. 5 is a perspective view of a foil pack containing lubricating gel as provided in the kit.

FIG. 5 shows a foil package 52 containing a gel for lubricating the catheter. The foil pack 52 may be torn at one edge, the gel squeezed onto a sterile field, and the catheter tip inserted into the gel for lubrication.

Figure 6A:
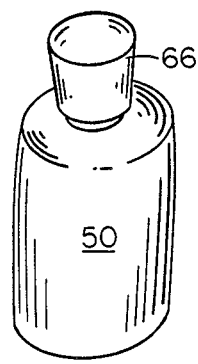
FIGS. 6A and 6B are perspective views of a disposable bottle containing water as provided in the kit.
Figure 6B:
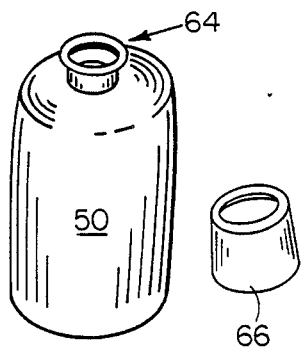

FIGS. 6A and 6B show a water bottle 50. Each bottle 50 includes a mouth 64 and a cap 66 cooperatively configured with the mouth for covering the bottle. Before use, a water tight and nonresealable seal is provided between the mouth 64 and cap 66. Once the cap 66 has been removed for use of the bottle 50, the cap and mouth 64 can not thereafter be resealed to form a water tight seal over the bottle. This minimizes the risk that a contaminated bottle will be reused in subsequent procedures.

Figure 7:
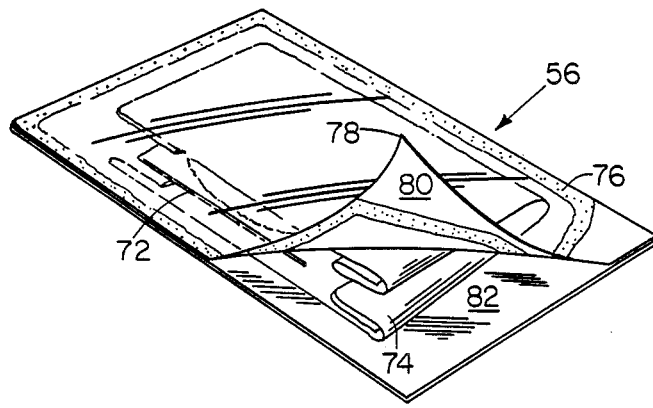
FIG. 7 is a perspective view of a sealed pouch for holding an envelope. The envelope holds a pair of surgical gloves and a folded bag. The folded bag in turn holds a suction catheter. As shown, the pouch has been partially opened.
Figure 8:
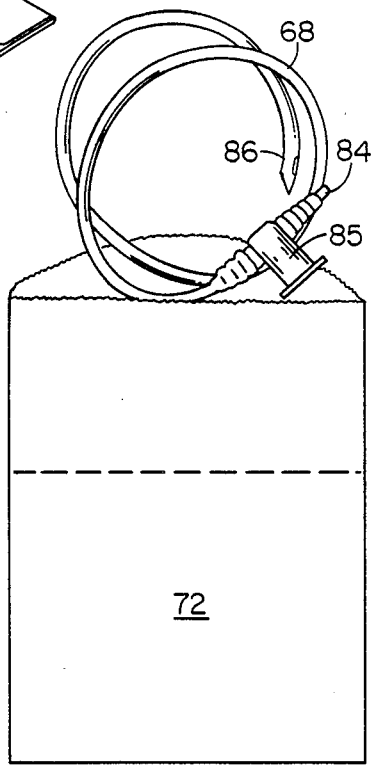
FIG. 8 is a plan view of the bag for holding the suction catheter, the bag having been removed from the sealed pouch shown in FIG. 7. As shown, the bag has been opened and the suction catheter removed.
Figure 9:
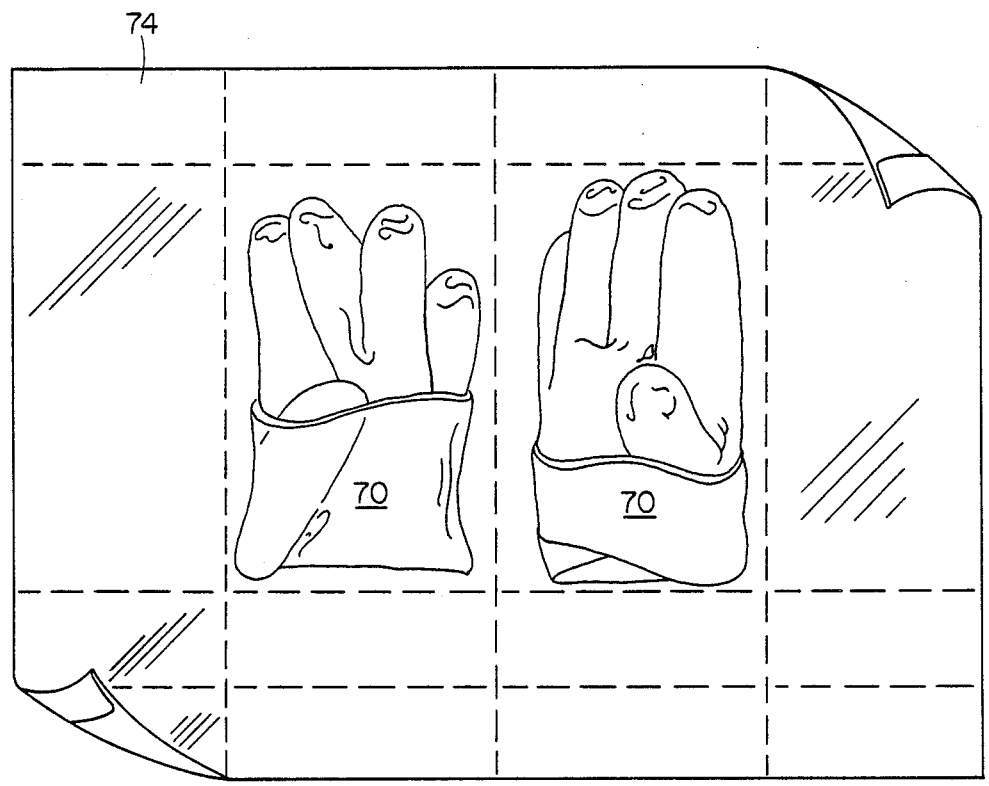
FIG. 9 is a plan view of the envelope containing the surgical gloves. As shown, the envelope has been unfolded to reveal the gloves.

FIG. 7 shows a sealed pouch 56 containing a paper envelope 74 which holds a suction catheter 68 (see FIG. 8) and a pair of surgical gloves 70 (see FIG. 9). As shown in FIG. 7, the pouch 56 has been partially opened. A folded over bag 72 is provided for holding the suction catheter within the pouch 56. Envelope 74 holds the bag 72 and the pair of surgical gloves within the pouch 56.

Sealed pouch 56 includes a pressed seal 76 proximate the peripheral edge of the pouch. Before use, the pouch is thus sealed for preventing contamination of the catheter and surgical gloves. When the technician desires to use the catheter and gloves, the pouch 56 may be peeled apart by grasping an edge 78 of the pouch and pulling the upper section 80 away from the lower section 82, thus releasing seal 76. The bag 72 and envelope 74 can thereafter be removed from pouch 56.

As shown in FIG. 8, once the bag 72 has been removed from the pouch, the bag may be unfolded and the suction catheter 68 may be removed for use. Similarly, as shown in FIG. 9, the envelope 74 can be unfolded and the pair of gloves 70 removed for use. Preferably, envelope 74 is provided in the pouch 56 in sterile condition. In this embodiment, the envelope 74 can be unfolded and used as a sterile field or drape during the suctioning procedure. Thus, the technician can place supplies on the drape 74 while performing the suctioning procedure.

As herein described, a preferred embodiment of the kit conveniently provides sufficient supplies for performing eight suctioning procedures. The following procedures for use of the kit are recommended.

For nasal suctioning, the kit 20 should be placed on a flat level surface near the work area. The cover 24 should be lifted to open the kit 20. The technician should remove one bottle 50 of water, one sealed pouch 56, and one foil pack 52 of lubricating gel. The kit 20 should then be closed and set aside. The foil pack 52 should be opened by tearing the pack at the appropriate edge. The bottle 50 of water should be opened by sharply snapping the cap 66 upward to break the seal. The catheter 68 and gloves 70 should be removed from the pouch 56 and the gloves placed on the technician's hands. The gel should be squeezed onto a sterile field, such as the unfolded envelope 74. The unfolded envelope 74 may be conveniently used as a sterile drape to place all supplies on during the procedure.

The appropriate end 84 of the catheter 68 should then be connected to a connecting tubing leading to a suction unit. The insertion tip 86 of the catheter 68 should then be dipped into the gel for lubrication, and the catheter thereafter advanced into the body passage to be suctioned. Suctioning may then be commenced by obstructing the opening on control valve 85.

After suctioning of the passage is completed, the catheter 68 may be removed from the passage and the tip 86 placed in the open bottle of water. Suctioning should be continued until the water is completely evacuated, thereby cleansing the connecting tubing and suction unit. The used supplies, such as the pouch, envelope, bag, bottle, bottle cap, gloves, catheter, and foil pack should then be discarded.

For tracheostomy suctioning, similar procedures should be followed, except that one or more saline solution ampules 54 should be removed from the kit 20 for use, and lubricating gel is generally not needed so no foil pack need be removed. After the catheter 68 is connected to a connecting tubing of a suction unit, the insertion tip 86 should be dipped into the sterile water for lubrication. The catheter 68 may then be advanced into the body passage to be suctioned.

If needed, saline solution from an ampule 54 may be dispersed into the area to be suctioned prior to insertion of the catheter 68 by snapping cap 60 off of nozzle 58 and squeezing body portion 57. Thereafter, the catheter 68 should be inserted into the body passage and suctioning commenced. After suctioning is completed, the catheter 68 should be removed and the tip 86 placed in the open bottle of water to cleanse the connecting tubing and suction unit. The used supplies, such as the pouch, envelope, bag, bottle, bottle cap, ampule, ampule cap, gloves, and catheter should then be discarded.

The instant invention has been disclosed in connection with specific embodiments. However, it will be apparent to those skilled in the art that variations from the illustrated embodiment may be undertaken. For example, although eight supply units in each kit may be the preferred number, any number of supply units may be selected, e.g. two, four, six, twelve, or any other number. These and other variations are considered within the spirit and scope of the invention.

What is claimed is:

1. A kit for use in performing a suctioning procedure, comprising:
   a tray; and
   suctioning supplies, including
      a pair of surgical gloves;
      an ampule containing a saline solution;
      a suction catheter;
      a lubricating gel; and
      a disposable bottle containing water;
   the suctioning supplies being removably disposed within the tray.

2. The kit of claim 1, wherein the tray includes compartments cooperatively configured to hold the suctioning supplies and the suctioning supplies are removably disposed within the compartments.

3. The suctioning kit of claim 2, further comprising a cover cooperatively configured with the tray for covering the tray.

4. The kit of claim 3, wherein the cover is hinged to the tray.

5. The kit of claim 3, further comprising a handle for carrying the kit.

6. The kit of claim 1, wherein the surgical gloves, saline solution, suction catheter, lubricating gel, and water are sterile.

7. The kit of claim 6, further comprising a sealed pouch for holding the gloves.

8. The kit of claim 6, further comprising a sealed pouch for holding the catheter.

9. The kit of claim 6, further comprising a sealed pouch for collectively holding the catheter and the gloves.

10. The kit of claim 1, wherein the disposable bottle containing sterile water includes:
    a mouth;
    a cap cooperatively configured with the mouth for covering the bottle; and
    a water tight and nonresealable seal between the mouth and the cap.

11. The kit of claim 1, further comprising a foil pack for holding the lubricating gel.

12. A kit for use in performing a series of suctioning procedures, comprising:
    a tray; and
    a series of supply units, each supply unit comprising suctioning supplies including
      a pair of surgical gloves;
      an ampule containing a saline solution;
      a suction catheter;
      a lubricating gel; and
      a disposable bottle containing water;
    the supply units being removably disposed within the tray.

13. The kit of claim 12, wherein the tray includes compartments cooperatively configured to hold the supply units and the supply units are removably disposed within the compartments.

14. The kit of claim 12, wherein the number of supply units is eight.

15. The kit of claim 12, further comprising a cover cooperatively configured with the tray for covering the tray.

16. The kit of claim 15, wherein the cover is hinged to the tray.

17. The kit of claim 15, further comprising a handle for carrying the kit.

18. The kit of claim 12, wherein the surgical gloves, saline solution, suction catheter, lubricating gel, and water of each supply unit are sterile.

19. The kit of claim 18, further comprising a sealed pouch for holding each pair of gloves.

20. The kit of claim 18, further comprising a sealed pouch for holding each catheter.

21. The kit of claim 18, further comprising a sealed pouch for collectively holding the pair of gloves and the catheter in each supply unit.

22. The kit of claim 12, wherein each disposable bottle containing sterile water includes:
    a mouth;
    a cap cooperatively configured with the mouth for covering the bottle; and
    a water tight and nonresealable seal between the mouth and the cap.

23. The suctioning kit of claim 12, each supply unit further comprising a foil pack for holding the lubricating gel.

24. The suctioning kit of claim 7, 8, 9, 19, 20, or 21, wherein the sealed pouch includes a sterile drape.

25. The kit of claim 3 or 15, wherein the cover includes recesses cooperatively configured to accommodate the suctioning supplies when the kit is closed.

26. The kit of claim 4 or 16, wherein the tray and cover each integrally include a handle section, the handle sections being cooperatively configured such that they join to form a handle upon closing the kit.

27. The kit of claim 26, wherein the handle sections include means for releasably locking the tray and cover in a closed position.

* * * * *